(12) United States Patent
Li et al.

(10) Patent No.: US 11,116,189 B2
(45) Date of Patent: Sep. 14, 2021

(54) EGG COLLECTING DEVICE FOR BLACK SOLDIER FLIES AND ITS OVIPOSITION PLATE SET

(71) Applicant: Guangzhou Unique Biotechnology Co., Ltd., Guangdong (CN)

(72) Inventors: Chujun Li, Guangdong (CN); Wenfeng Hu, Guangdong (CN); Xu Pang, Guangdong (CN); Boyu Chen, Guangdong (CN); Dou Hu, Guangdong (CN)

(73) Assignee: Guangzhou Unique Biotechnology Co., Ltd., Guangzhou (CN)

( * ) Notice: Subject to any disclaimer, the term of this patent is extended or adjusted under 35 U.S.C. 154(b) by 460 days.

(21) Appl. No.: 16/041,758

(22) Filed: Jul. 21, 2018

(65) Prior Publication Data

US 2019/0133096 A1     May 9, 2019

(30) Foreign Application Priority Data

Nov. 8, 2017  (CN) .......................... 201721501056.0

(51) Int. Cl.
*A01K 67/033* (2006.01)

(52) U.S. Cl.
CPC .................. *A01K 67/033* (2013.01)

(58) Field of Classification Search
CPC ...... A01K 67/033; A01K 67/00; A01K 29/00; A01K 1/00; G01N 2015/0261
See application file for complete search history.

(56) References Cited

U.S. PATENT DOCUMENTS

| 2,670,562 A | * | 3/1954 | Gould ................... | A01K 97/04 |
| | | | | 43/55 |
| 3,191,199 A | * | 6/1965 | Barnes, Jr. ............. | A01K 47/00 |
| | | | | 449/4 |

(Continued)

FOREIGN PATENT DOCUMENTS

CA            2530647 A1  *  7/2006  ........... A01K 67/033

OTHER PUBLICATIONS

Ewusie, E.A. et. al. "The black soldier fly, *Hermetia illucens* (Diptera: Stratiomyidae): Trapping and culturing of wild colonies in Ghana" 2019 (Year: 2019).*

(Continued)

*Primary Examiner* — Magdalena Topolski
*Assistant Examiner* — Katelyn T Truong

(57) ABSTRACT

The present invention discloses an egg collecting device for black soldier flies and its oviposition plate set, comprising at least two oviposition plates which can be reused; the oviposition plates are positioned in an overlapping manner, and a gap is provided between surfaces of adjacent oviposition plates for the oviposition of black soldier flies. The egg collecting device for black soldier flies comprises a box containing oviposition-inducing material, a screen board, and the oviposition plate mentioned above; the box containing oviposition-inducing material is covered with the screen board, and the oviposition plate set is provided on the screen board. The present invention could simulate an oviposition environment according to the oviposition habits of black soldier flies, and it better induces of the oviposition of black soldier flies, providing a good foundation for large-scale, commercial oviposition of black soldier flies.

8 Claims, 6 Drawing Sheets

(56) References Cited

U.S. PATENT DOCUMENTS

| | | | | | |
|---|---|---|---|---|---|
| 3,267,497 | A | * | 8/1966 | Dority | A01K 49/00 449/4 |
| 3,936,894 | A | * | 2/1976 | Barber | A01K 49/00 449/4 |
| 5,372,535 | A | * | 12/1994 | Mills | A01K 47/00 449/36 |
| 5,403,226 | A | * | 4/1995 | Trafford | A01K 47/02 449/4 |
| 6,130,084 | A | * | 10/2000 | Endencia | A01K 67/033 119/6.5 |
| 8,465,340 | B1 | * | 6/2013 | Allan | A01K 67/033 449/4 |

OTHER PUBLICATIONS

Ephraim, Tayne "Black Soldier Flies" Jul. 16, 2016, oivietnam.com (Year: 2016).*
STIC Non patent document search report (dated 2021).*
Dinh, Quoc-Huy Nguyen, How to collect black soldier fly eggs Jan. 18, 2017 (Year: 2017).*
Boaru, Anca et. al "The use of various oviposition structures for the black soldier fly, *Hermetia illucens* L. (Diptera: Stratiomydae) in improving the reproductive process in captivity" ABAH Bioflux 2019 vol. 11 issue 1 (Year: 2019).*
Ewag "Black Soldier Fly Biowaste Processing" (pp. 1,3, and 46-47), 2017 (Year: 2017).*

\* cited by examiner

EGG COLLECTING DEVICE FOR BLACK SOLDIER FLIES AND ITS OVIPOSITION PLATE SET

CROSS REFERENCE TO RELATED APPLICATIONS

The present application claims the benefit of Chinese Utility Model Application No. 201721501056.0 filed on Nov. 8, 2017. All the above are hereby incorporated by reference.

FIELD OF THE INVENTION

The present invention relates to a biological collecting device and, in particular, to an egg collecting device for black soldier flies and its oviposition plate set.

BACKGROUND OF THE INVENTION

The black soldier fly is a dipterous insect that belongs to the family of Stratiomyidae. Wild female black soldier flies usually lay their eggs in fine gaps formed between grasses and branches that are close to water or food source or inside muddy caves. Captively bred adult black soldier flies lay their eggs in egg collecting devices which induces oviposition. An egg collecting device of the prior art uses corrugated papers as its oviposition plates: corrugated papers for oviposition are stacked on a screen board, adult black soldier flies are induced to lay their eggs on these corrugated papers. However, there are some drawbacks:

Firstly, in the breeding process, water is sprayed into a breeding greenhouse for cooling or for water replenishment. This leads to the softening of corrugated papers as water is inevitably sprayed onto them. As a result, they fail at attracting a substantial number of female black soldier flies; the survival rate for laid eggs is also lowered.

Secondly, corrugated papers are designed for packaging instead of insect oviposition; the size of their holes cannot be adjusted. Eggs, especially those being laid in small holes of the corrugated papers are difficult to remove for processing. Weighing and quantitative analysis are also inconvenient.

Thirdly, corrugated papers are relatively expensive and cannot be reused, resulting in higher oviposition costs.

SUMMARY OF THE INVENTION

To solve the problems mentioned above, the present invention provides an egg collecting device for black soldier flies and its oviposition plate set, which can simulate an oviposition environment according to the oviposition habits of black soldier flies. The egg collecting device and its oviposition plate set can be reused and is cost effective; they are able to attract more black soldier flies for oviposition, which is advantageous to egg collection.

The present invention thus provides an oviposition plate set for black soldier flies, comprising at least two oviposition plates which can be reused; the oviposition plates are positioned in an overlapping manner, and a gap is provided between surfaces of adjacent oviposition plates for the oviposition of black soldier flies.

Furthermore, the oviposition plate is a trapezoidal-shaped plate that comprises an upper surface, a lower surface, and inclined surfaces; the upper surface is smaller in size than the lower surface and parallel to the lower surface; said gap is formed between the inclined surface and the lower surface of two adjacent trapezoidal boards.

Furthermore, the oviposition plate is cuboid-shaped; said gap is formed between two adjacent oviposition plates which are separated by separators.

Furthermore, the separators are drawing pins, the drawing pins are arranged at two ends of a surface of the oviposition plate; the surface provided with the drawing pins is positioned upwards.

Furthermore, each of the oviposition plates is covered with an outer cover; the overlapping manner in which the oviposition plates are positioned is fixed by a binding device.

Furthermore, the outer cover is a cloth bag, black cloth or plastic film.

Furthermore, the binding device is a rubber band or a string.

Furthermore, the oviposition plate set further comprises a piece of continuous cloth, a plurality of pockets is provided on the continuous cloth; each of the oviposition plates is provided inside one of the pockets, and then positioned in an overlapping manner.

In addition, the present invention also provides an egg collecting device for black soldier flies, comprising a box containing oviposition-inducing material, a screen board, and the oviposition plate set mentioned above; the box containing oviposition-inducing material is covered with the screen board, and the oviposition plate set is provided on the screen board.

Furthermore, the box containing oviposition-inducing material is in the shape of a cuboid, four upper vertices of the cuboid are respectively connected to a rope, and the ropes are all tied to one hook.

Comparing with the prior art, the beneficial effects of the present invention are as follows:

1. The egg collecting device of the present invention can simulate an oviposition environment according to the oviposition habits of black soldier flies; the device better induces of the oviposition of black soldier flies, and the oviposition sites chosen by female flies are more concentrated. As a result, the amount of eggs laid per unit space is increased; the rate of oviposition in undesired sites is reduced. The egg collecting device of the present invention provides a good foundation for large-scale, commercial oviposition of black soldier flies.

2. The eggs of black soldier flies are collected with the oviposition plate of the present invention, which can be reused. Furthermore, the oviposition plate set and the egg collecting device can also be reused. This leads to the lowering of costs, the reduction of losses caused by the damage of oviposition plates, and is good for the environment. In addition, water can be sprayed onto the oviposition plate without the oviposition plate turning soft as a result. Many gaps are present on the surfaces of the oviposition plates, which attract more female adult flies, thereby improving oviposition rate.

3. By providing an outer cover onto the oviposition plate, the eggs can be directly wrapped and collected; the step of egg scraping can be omitted, which reduces the cost of labor and leads to a simpler and more efficient egg collection process.

REFERENCE NUMERALS

Figure 1A:
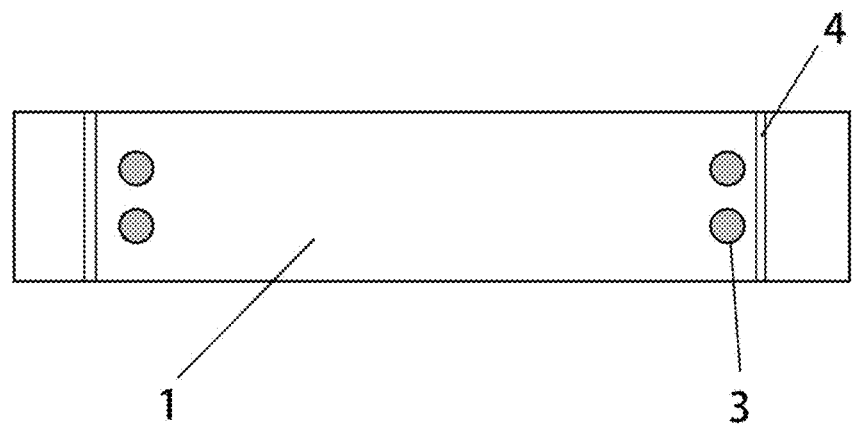
FIG. 1A is a top view of an oviposition plate set according to embodiment 1 of the present invention.

1—oviposition plate; 21—cloth bag; 22—black cloth; 23—plastic film; 3—drawing pin; 4—binding device; 5—box containing oviposition-inducing material; 6—screen board; 7—rope; 8—hook; 9—gap; 10—oviposition plate set.

DETAILED DESCRIPTION OF THE ILLUSTRATED EMBODIMENTS

The technical solutions of the present invention will be clearly and fully described hereafter with reference to the accompanying drawings and embodiments. It is obvious that the described embodiments are merely a part, not all, of the embodiments of the present invention. Based on the embodiments of the present invention, all other embodiments obtained by those of ordinary skill in the art without any creative efforts shall fall within the protection scope of the present invention.

FIGS. 1A-1C, 2A-2C, 3A-3B, 4A-4C, and 5A-5C show an oviposition plate set for black soldier flies, comprising at least two oviposition plates 1 which can be reused; the oviposition plates 1 are positioned in an overlapping manner, and a gap 9 is provided between surfaces of adjacent oviposition plates 1 for the oviposition of black soldier flies. The material of the oviposition plate 1 can be selected from materials that are likely to attract the oviposition of black soldier flies and can be reused, such as wood, metal or plastic. As oviposition plate 1 can be reused, the oviposition plate set can also be reused consequentially. This leads to the lowering of costs, the reduction of losses caused by the damage of oviposition plates, and is good for the environment. In addition, water can be sprayed onto the oviposition plate without the oviposition plate turning soft as a result. Many gaps are present on the surfaces of the oviposition plates, which attract more female adult flies, thereby improving oviposition rate.

The oviposition plate 1 of the embodiments of the present invention could be a trapezoidal-shaped or a cuboid-shaped plate. When the oviposition plate 1 is a trapezoidal-shaped plate, it comprises an upper surface, a lower surface, and inclined surfaces; the upper surface is smaller in size than the lower surface and parallel to the lower surface; said gap 9 is formed between the inclined surface and the lower surface of two adjacent trapezoidal plates. When the oviposition plate 1 is a cuboid-shaped plate, said gap 9 is formed between two adjacent oviposition plates which are separated by separators. These separators are arranged at two ends of a surface of the cuboid-shaped oviposition plate 1. The separators are drawing pins 3, which are arranged at two ends of a surface of the oviposition plate; the surface provided with the drawing pins 3 is positioned upwards. The separation distance between two adjacent oviposition plates 1 is 2-5 mm.

Preferred embodiments of the oviposition plate set are described hereafter.

Embodiment 1

Figure 1B:
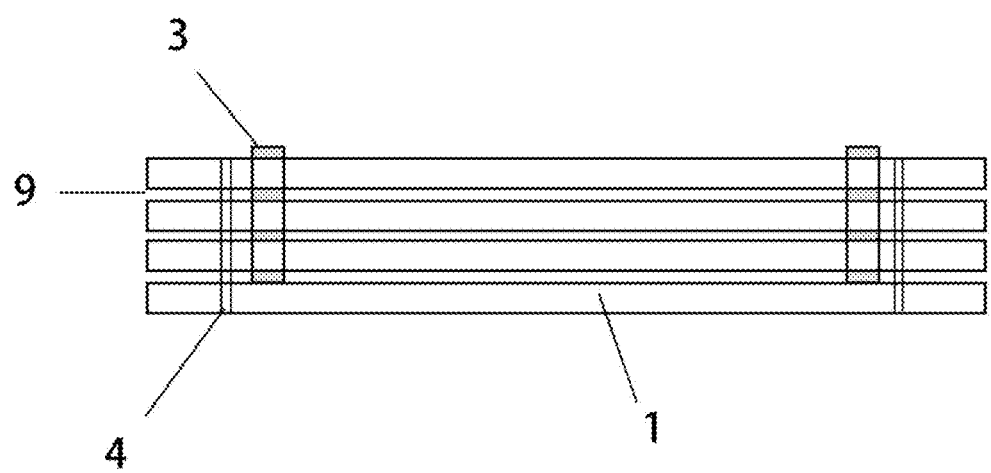
FIG. 1B is a front view of an oviposition plate set according to embodiment 1 of the present invention.
Figure 1C:
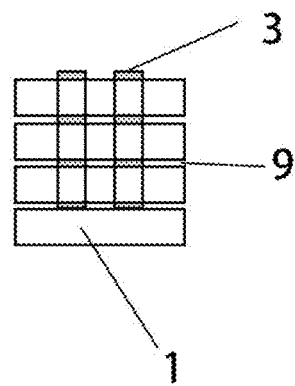
FIG. 1C is a side view of an oviposition plate set according to embodiment 1 of the present invention.

As shown in FIGS. 1A-1C, the dimension of the oviposition plate 1 of the present embodiment is 240×50×10 mm. Drawing pins 3 are provided on two ends of a surface of the oviposition plate 1. The radius of the head of the drawing pin 3 is 11 mm, and the thickness of the head of the drawing pin 3 is 2 mm. The surfaces of oviposition plates 1 provided with drawing pins 3 are positioned upwards. The oviposition plates 1 are positioned in an overlapping manner, fixed by a rubber band, together forming the oviposition plate set.

Embodiment 2

Figure 2A:
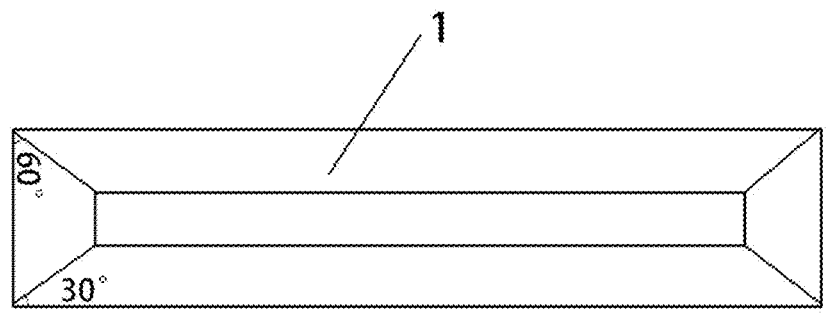
FIG. 2A is a top view of an oviposition plate set according to embodiment 2 of the present invention.
Figure 2B:
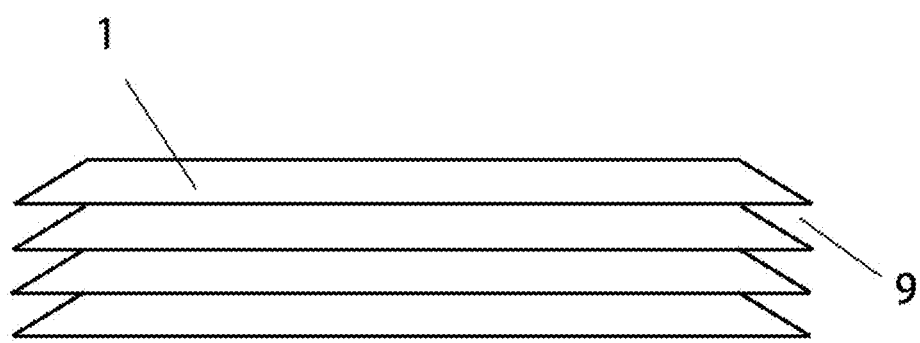
FIG. 2B is a front view of an oviposition plate set according to embodiment 2 of the present invention.
Figure 2C:
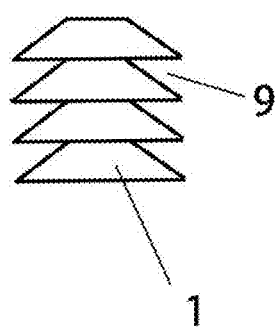
FIG. 2C is a side view of an oviposition plate set according to embodiment 2 of the present invention.

As shown in FIGS. 2A-2C, the oviposition plate 1 is a trapezoidal-shaped plate, which comprises an upper surface, a lower surface, and four inclined surfaces. Two of the inclined surfaces have an inclination angle of 60°; the other two inclined surfaces have an inclination angle of 30°. The upper surface is smaller in size than the lower surface and parallel to the lower surface. The dimension of the upper surface is 200×10 mm; the dimension of the lower surface is 240×50 mm. The oviposition plates 1 are positioned in an overlapping manner, fixed by a rubber band, together forming the oviposition plate set. It should be noted that in the present embodiment, the overlapping positioning of the oviposition plates 1 can also be maintained without using any binding device.

As female adult black soldier flies landed onto the oviposition plate sets described in embodiments 1 and 2, they laid their eggs on oviposition plates 1. After oviposition plates 1 were fully loaded with eggs, the binding device 4 was untied, and the oviposition plates 1 were removed one by one. It was found that the edges of two oviposition plates 1 were covered with eggs. A scraper made of wood, stainless steel or rubber was used to scrape off the eggs. The cleaned oviposition plates 1 were then rinsed with water and sterilized with alcohol. After drying, they could be repeatedly used. Also, in the egg collecting device for black soldier flies, the dimension of the box containing oviposition-inducing material 5 used in combination with the oviposition plate set described in embodiments 1 and 2 was 1000×500×200 mm.

Embodiment 3

Figure 3A:
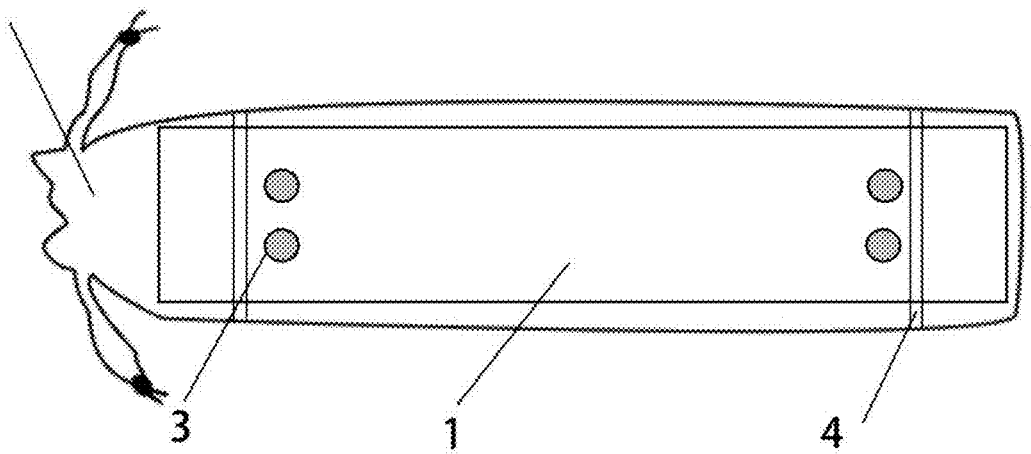
FIG. 3A is a top view of an oviposition plate set according to embodiment 3 of the present invention.
Figure 3B:
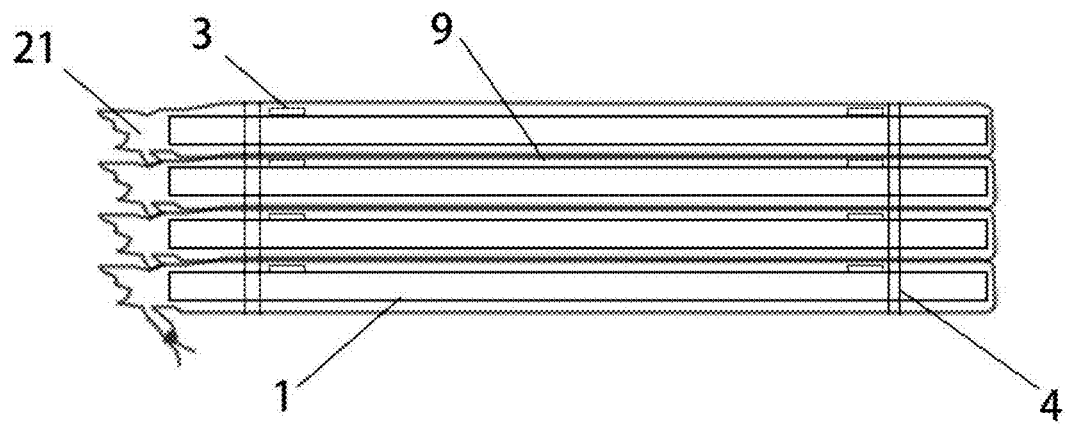
FIG. 3B is a front view of an oviposition plate set according to embodiment 3 of the present invention.

As shown in FIGS. 3A-3B, the dimension of the oviposition plate 1 of the present embodiment is 300×80×10 mm.

Drawing pins 3 are provided on two ends of a surface of the oviposition plate 1. The radius of the head of the drawing pin 3 is 11 mm, and the thickness of the head of the drawing pin 3 is 5 mm. The surfaces of oviposition plates 1 provided with drawing pins 3 are positioned upwards. Each of the oviposition plate 1 is covered with an outer cover, which is a cloth bag 21. One end of the cloth bag 21 is fastened. The oviposition plates 1 covered with cloth bags 21 are positioned in an overlapping manner, fixed by a rubber band, together forming the oviposition plate set. In addition, the dimension of the box containing oviposition-inducing material 5 used in combination with the oviposition plate set of the present embodiment is 2000×800×200 mm.

Embodiment 4

Figure 4A:
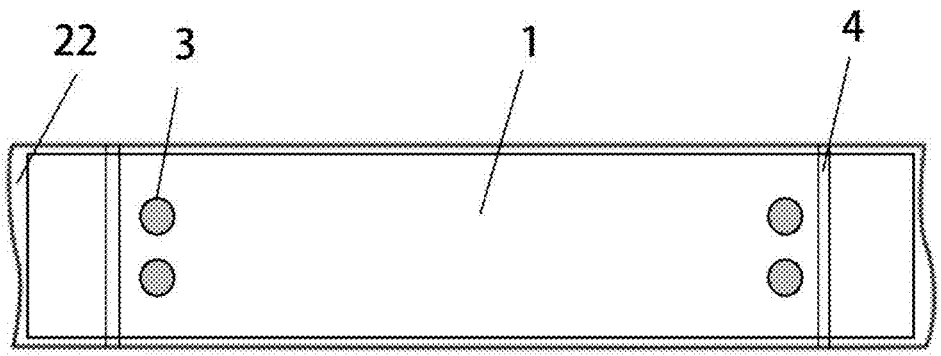
FIG. 4A is a top view of an oviposition plate set according to embodiment 4 of the present invention.
Figure 4B:
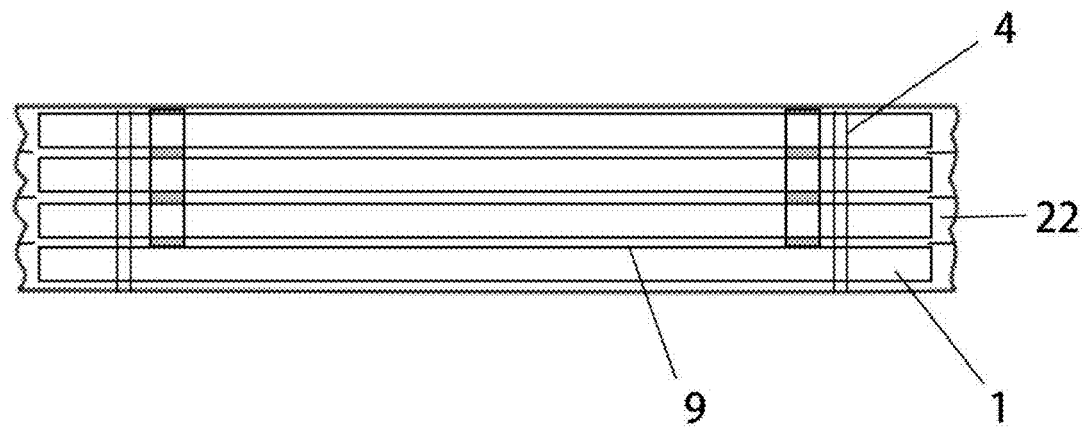
FIG. 4B is a front view of an oviposition plate set according to embodiment 4 of the present invention.
Figure 4C:
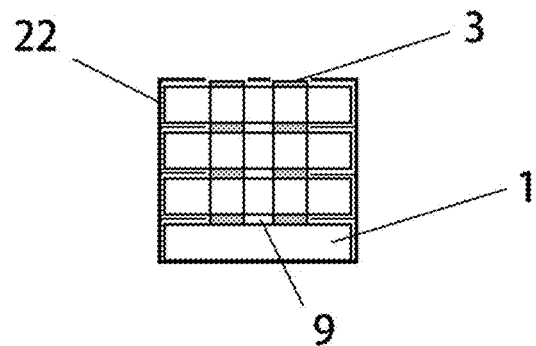
FIG. 4C is a side view of an oviposition plate set according to embodiment 4 of the present invention.

As shown in FIGS. 4A-4C, the dimension of the oviposition plate 1 of the present embodiment is 300×80×10 mm. Drawing pins 3 are provided on two ends of a surface of the oviposition plate 1. The radius of the head of the drawing pin is 11 mm, and the thickness of the head of the drawing pin is 5 mm. The surfaces of oviposition plates 1 provided with drawing pins 3 are positioned upwards. Each of the oviposition plate 1 is covered with an outer cover, which is a piece of black cloth 22. Regarding the oviposition plate set, there are two possible arrangements: (1) each of the oviposition plate 1 is covered with a piece of black cloth 22; these oviposition plates are positioned in an overlapping manner, fixed by a rubber band, together forming the oviposition plate set. (2) Only one piece of black cloth 22 is used, and it is positioned on the surface of all oviposition plates 1. When the oviposition plates 1 are positioned in an overlapping manner, the whole piece of black cloth 22 is folded into an "S" shape accordingly, together forming the oviposition plate set. In addition, the dimension of the box containing oviposition-inducing material 5 used in combination with the oviposition plate set of the present embodiment is 2000×800×200 mm.

Embodiment 5

Figure 5A:
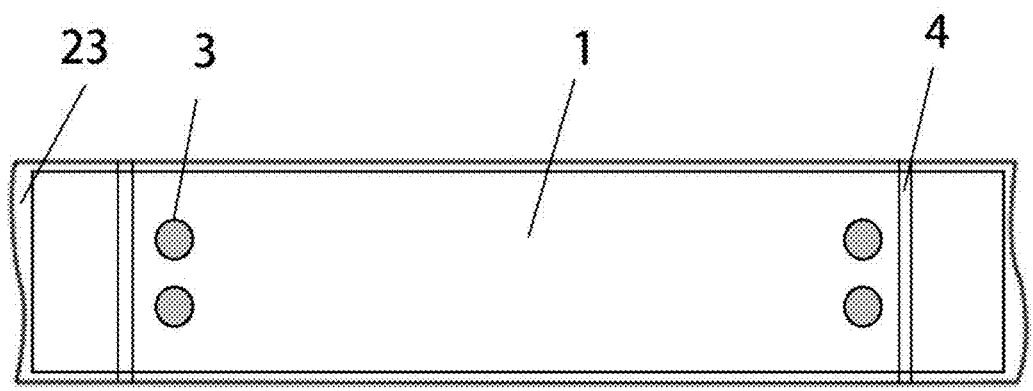
FIG. 5A is a top view of an oviposition plate set according to embodiment 5 of the present invention.
Figure 5B:
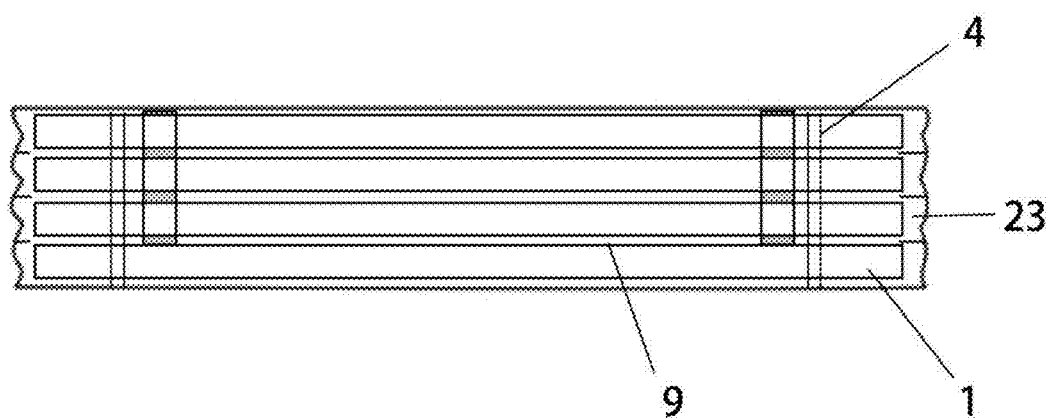
FIG. 5B is a front view of an oviposition plate set according to embodiment 5 of the present invention.
Figure 5C:
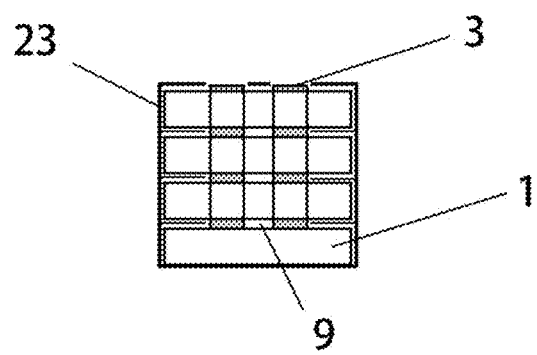
FIG. 5C is a side view of an oviposition plate set according to embodiment 5 of the present invention.

As shown in FIGS. 5A-5C, the dimension of the oviposition plate 1 of the present embodiment is 240×80×10 mm. Drawing pins 3 are provided on two ends of a surface of the oviposition plate 1. The radius of the head of the drawing pin is 11 mm, and the thickness of the head of the drawing pin is 3 mm. The surfaces of oviposition plates 1 provided with drawing pins 3 are positioned upwards. Each of the oviposition plate 1 is covered with an outer cover, which is a piece of plastic film 23. The plastic film 23 is disposable. One end of the plastic film 23 covering the oviposition plate 1 is heat-sealed. The oviposition plates 1 are positioned in an overlapping manner, fixed by a rubber band, together forming the oviposition plate set. In addition, the dimension of the box containing oviposition-inducing material 5 used in combination with the oviposition plate set of the present embodiment is 2500×900×200 mm.

In embodiments 3, 4 and 5, both the cloth bag 21 and the black cloth 22 are made of non-woven fabric. Female black soldier flies which landed on the oviposition plate set laid their eggs on the cloth bag 21, the black cloth 22 or the plastic film 23. After the cloth bag 21, the black cloth 22 or the plastic film 23 was covered with eggs, the oviposition plate set was removed from the egg-collecting device. The binding device 4 was untied, and the oviposition plates 1 were then separated from the cloth bag 21, the black cloth 22 or the plastic film 23 and spread out. Eggs could be found covered on the edges of the cloth bag 21, the black cloth 22 and the plastic film 23. The cloth bag 21 was untied, turned over and tightened again, forming an insect egg bag. Alternatively, the cloth bag 21, the black cloth 22 and the plastic film 23 were unfolded; the eggs on the cloth bag 21, the black cloth 22 and the plastic film 23 were shaken off and removed. This effectively protects the eggs, and the step of scraping oviposition plates 1 could be omitted, which reduces the damages to the eggs and oviposition plates 1 while effectively collecting all of the eggs. The cleaned oviposition plates 1 were rinsed with water and sterilized with alcohol. After drying, they were again covered with the cloth bag 21, the black cloth 22 or the plastic film 23 and ready to be used again.

Embodiment 6

The dimension of the oviposition plate is 300×80×10 mm, 240×50×10 mm or 240×80×10 mm. Drawing pins are provided on two ends of a surface of the oviposition plate. The radius of the head of the drawing pin is 11 mm, and the thickness of the head of the drawing pin is 5 mm or 3 mm. The surfaces of oviposition plates provided with drawing pins are positioned upwards. A piece of continuous cloth is used, a plurality of pockets is provided on the continuous cloth; each of the oviposition plates is provided inside a pocket, and then positioned in an overlapping manner, together forming the oviposition plate set. In addition, the dimension of the box containing oviposition-inducing material used in combination with the oviposition plate set of the present embodiment is 2000×800×200 mm, 1000×500×200 mm, or 2500×900×200 mm. The continuous cloth is made of non-woven fabric. Female black soldier flies which landed on the oviposition plate set laid their eggs on the continuous cloth. After the continuous cloth was covered with eggs, the oviposition plate set was removed. The continuous cloth was unfolded, and each oviposition plate 1 was removed from the pocket. Eggs could be found covered on the edges of the continuous cloth were covered with eggs. The continuous cloth was turned over and tightened again, forming an insect egg bag. Alternatively, the continuous cloth was unfolded; the eggs on the continuous cloth were shaken off and removed. This effectively protects the eggs, and the step of scraping oviposition plates can be omitted, which reduces the damages to the eggs and oviposition plates while effectively collecting all of the eggs. After drying, they were again covered with the continuous cloth and ready to be used again.

Figure 6:
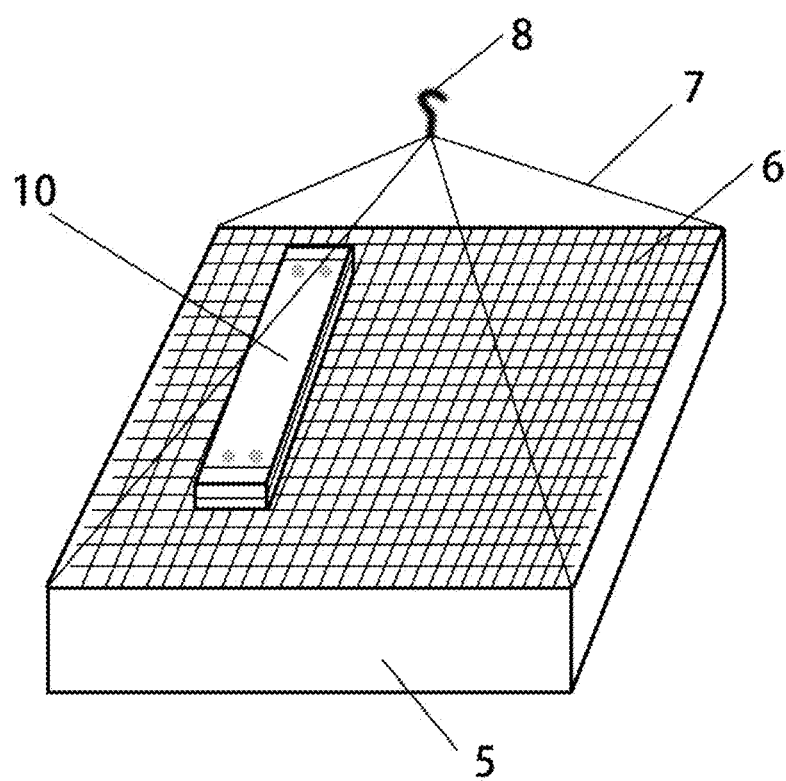
FIG. 6 is a schematic diagram of the overall structure of an egg collecting device for black soldier flies according to embodiments of the present invention.

FIG. 6 illustrates an egg collecting device for black soldier flies, comprising a box containing oviposition-inducing material 5, a screen board 6, and an oviposition plate set 10. The box containing oviposition-inducing material 5 is covered with the screen board 6, and the oviposition plate set 10 is provided on the screen board 6. The dimension of the box containing oviposition-inducing material 5 is 2000×800×200 mm, 1000×500×200 mm, or 2500×900×200 mm. The oviposition-inducing material prepared was placed in the box containing oviposition-inducing material 5, covered with the screen board 6, and the oviposition plate set 10 is directly positioned on the screen board 6. A plurality of oviposition plate sets 10 could be positioned on the screen board 6. The egg collecting device is then placed in an oviposition room; a plurality of egg collecting devices could be placed in the oviposition room. However, taking into account the oviposition habits of black soldier flies, it is preferable to place two egg collecting devices in one oviposition room. The box containing oviposition-inducing material 5 is in the shape of a cuboid. The four upper vertices of the cuboid are respectively connected with a rope 7, and the ropes 7 are tied to a hook 8. For overall aesthetics and practicality, the space enclosed by the four ropes 7 and the upper surface of the screen board 6 resembles the shape of a pyramid shape, and the hook 8 is provided at the apex of the pyramid. In this way, the egg collecting devices could be hung, allowing efficient use of three-dimensional space.

In view of the above, the egg collecting devices and their oviposition plate sets of the embodiments above could lower costs and reduce losses caused by the damage of oviposition plates. They are good for the environment as their oviposition plates 1 could be reused. By employing an outer cover, the step of egg scraping can be omitted. The egg collecting device of the present invention can simulate an oviposition environment according to the oviposition habits of black soldier flies. It better induces the oviposition of black soldier flies, and the oviposition sites chosen by female flies are more concentrated. As a result, the amount of eggs laid per unit space is increased, providing a good foundation for large-scale, commercial oviposition of black soldier flies.

The above description only refers to preferred embodiments of the present invention. It should be pointed out that for a person of ordinary skill in the art, improvements and substitutions could be made without departing from the technical principles of the present invention. Such improvements and substitutions should be regarded as within the protection scope of the present invention.

What is claimed is:

1. An oviposition plate set for black soldier flies, comprising
    at least two reusable oviposition plates placed in an overlapping position, each of the at least two oviposition plates is cuboid-shaped; adjacent oviposition plates are separated by a separator, thereby forming a gap between the adjacent oviposition plates; the gap is for the oviposition of the black soldier flies; and
    a piece of cloth provided with a plurality of pockets, each of the at least two oviposition plates is placed in one of the pockets.

2. The oviposition plate set for black soldier flies according to claim 1, wherein each of the at least two oviposition plates is covered with an outer cover; the at least two oviposition plates are held in the overlapping position by a binding device.

3. The oviposition plate set for black soldier flies according to claim 2, wherein the outer cover is a cloth bag, a piece of black cloth or a plastic film.

4. An egg collecting device for black soldier flies, comprising
    a box containing oviposition-inducing material;
    a screen board; and
    the oviposition plate set according to claim 3;
    wherein the screen board covers the box, and the oviposition plate set is provided on the screen board.

5. An egg collecting device for black soldier flies, comprising
    a box containing oviposition-inducing material;
    a screen board; and
    the oviposition plate set according to claim 2;
    wherein the screen board covers the box, and the oviposition plate set is provided on the screen board.

6. The oviposition plate set for black soldier flies according to claim 2, wherein the binding device is a rubber band or a string.

7. An egg collecting device for black soldier flies, comprising
    a box containing an oviposition-inducing material;
    a screen board; and
    the oviposition plate set according to claim 1;
    wherein the screen board covers the box, and the oviposition plate set is provided on the screen board.

8. The egg collecting device for black soldier flies according to claim 7, wherein the box has a cuboid shape, four ropes are respectively attached to four upper vertices of the box, and the four ropes are all tied to one hook.

* * * * *